US005304354A

United States Patent [19]

Finley et al.

[11] Patent Number: 5,304,354
[45] Date of Patent: Apr. 19, 1994

[54] CATALYTIC CHEMICAL REACTION ASSEMBLY

[75] Inventors: Charles M. Finley, Arcadia; Charles L. Kissel, Anaheim, both of Calif.

[73] Assignee: Baker Hughes Incorporated, Houston, Tex.

[21] Appl. No.: 983,242

[22] Filed: Nov. 30, 1992

Related U.S. Application Data

[63] Continuation of Ser. No. 625,302, Dec. 7, 1990, abandoned.

[51] Int. Cl.$^5$ .............................................. B01J 8/06
[52] U.S. Cl. .................................... 422/196; 422/109; 422/130; 422/197; 422/199; 422/211; 422/240; 422/241
[58] Field of Search ............... 422/109, 130, 196, 197, 422/199, 211, 240, 241

[56] References Cited

U.S. PATENT DOCUMENTS

| 2,240,481 | 5/1941 | Aicher | 422/197 |
|---|---|---|---|
| 4,213,831 | 7/1980 | Hall et al. | 203/86 |
| 4,302,292 | 11/1981 | von Waclawiczek et al. | 422/199 |
| 4,400,465 | 8/1983 | Morihara et al. | 435/68.1 |
| 4,608,364 | 8/1986 | Grau | 514/4 |
| 4,701,440 | 10/1987 | Grau | 514/3 |
| 4,751,057 | 6/1988 | Westerman | 422/197 |
| 4,780,196 | 10/1988 | Alagy et al. | 422/197 |
| 4,916,212 | 4/1990 | Marhussen | 435/69.4 |
| 4,946,828 | 8/1990 | Marhussen | 514/3 |
| 4,959,351 | 9/1990 | Grau | 514/3 |
| 5,008,241 | 4/1991 | Markussen et al. | 514/3 |
| 5,028,586 | 7/1991 | Balschmidt et al. | 514/3 |
| 5,028,587 | 7/1991 | Dorschug et al. | 514/3 |

FOREIGN PATENT DOCUMENTS

2016614 10/1971 Fed. Rep. of Germany .

OTHER PUBLICATIONS

Blundell et al., *Advances in Protein Chemistry*, 26: 340–347 (Ed. Anifinsen, Edsall, Richards), 1972.
Weinert, M. et al., *Hoppe-Seyler's Z-Physiol. Chem.*, 352: 719–724, 1971.
Zahn et al., "Molecular Basis of Insulin-Action", 5th Anniversary Insulin Symposium, Indiana, Oct. 1971.
Smith, L., "Amino Acid Sequences of Insulin", Sec. III The Molecular Basis of Action, 5th Anniversary Insulin Symp. 1971.
Dayhoff, M., Atlas of Protein Sequence and Structure, vol. 5: 89–99, 1972.
Creighton, T., *Proteins*, Watt. Freeman & Co., 1984, p. 428.
Patent Abstracts of Japan, vol. 6, No. 54, (C-97) (932) Apr. 9, 1982, of JP 56-166937-A, Dec. 22, 1981.
Patent Abstracts of Japan, vol. 11, No. 193, (C-430) (2640) Jun. 20, 1987, of JP 62-19240-A, Jan. 28, 1987.
C. Z. Xing, et al., "Partial Oxidation of Propylene by a Tube Wall Catalytic Reactor," *Kagaku Kigaku Ronbunshu*, vol. 10, No. 4, pp. 439–445 (1984).

*Primary Examiner*—Timothy M. McMahon
*Attorney, Agent, or Firm*—Rosenblatt & Assoc.

[57] ABSTRACT

A catalytic chemical reactor of a sandwiched configuration is described. The reactor has at least one plate with a major surface and two minor ends opposite one another across the major surface. A plurality of reaction chambers are present in the plate, parallel to one another and the major surface, extending from one of the minor ends to the other. The reactor additionally comprises at least one heating panel adjacent and parallel to the flat plate. The plates may be configured in modular pairs with a heating panel in between each pair. The reactor is particularly adapted to produce organic chemicals, such as acrolein, in significant, but moderate quantities. Additionally, the reactor is of such a size that it is readily portable. Unusually, the reactor plates, or at least their inner surfaces, may be made from materials such as aluminum, tantalum, titanium, tungsten, niobium and mixtures thereof.

14 Claims, 4 Drawing Sheets

CATALYTIC CHEMICAL REACTION ASSEMBLY

This is a continuation of copending application Ser. No. 07/625,302 filed on Dec. 7, 1990 now abandoned.

FIELD OF THE INVENTION

The invention relates to chemical reactors, and more particularly, the invention relates, in one aspect, to chemical reactors which employ a catalyst and even more particularly to catalytic chemical reactors which may be portable.

BACKGROUND OF THE INVENTION

Chemical reactors are well known in the art and may take a number of different forms. For example, some of the well known types of reactors include, but are not limited to batch reactors, stirred tank reactors, continuous stirred tank reactors (CSTRs), tubular reactors, multiple-pass reactors, fixed bed reactors, fluidized bed reactors and spouted bed reactors. These last three are specific types of catalytic reactors.

Most commercial reactors are relatively large, on the order of tens of feet tall, which require that they remain permanent fixtures to the operating site. Chemical reaction devices which are portable most often refer to laboratory or bench scale equipment, which are not suitable for the production of large volumes of products. Skid- or trailer mounted reactors, are known, of course, where appreciable quantities of a certain material are required and it is also desired that the overall unit be modular or portable, but these tend not to be catalytic systems.

However, there remains a need for different kinds of portable catalytic chemical reactors which produce appreciable volumes of chemicals in good yields. It would be an additional advantage if the reactor were somewhat modular so that modules could be added to the system to adjust the capacity of the reactor system. A small reactor using aluminum tubes coated with copper as a catalyst was reported by Xing and Inoue, *Kagaku Kogaku Ronbunshu*, Vol. 10, No. 4, 439–45 (1984).

SUMMARY OF THE INVENTION

Accordingly, it is an object of the present invention to provide a chemical reactor useful in the volume production of products, which reactor may be portable.

It is another object of the present invention to provide a chemical reactor which may be considered as a module or cell and which may be readily interconnected in parallel with other reactors to increase the volume of product.

Another object of the present invention is to provide a chemical reactor having reaction chambers with surfaces that are relatively inert to oxidation reactions and their products.

In carrying out these and other objects of the invention, there is provided, in one form, a reactor for containing a catalyst suitable to facilitate a chemical reaction, where the reactor has at least one flat plate which, in turn, has a major surface, a first minor end, and a second minor end opposite the first minor end. Present within the flat plate are a plurality of reaction chambers oriented parallel to one another and parallel to the major surface, beginning at the first minor end at an inlet and terminating at the second minor end at an outlet. The chambers are for receiving a catalyst. The reactor additionally has at least one flat heating panel adjacent and parallel to the flat plate.

This invention provides a portable, self-contained system for generating dilute solutions of various products in significant quantities on-demand and on-site. With the system of this invention, the products are not produced and shipped in a concentrated liquid form, but instead are produced and used in a relatively short time on site in a dilute solution in a liquid compatible with the liquid to be treated.

The improved reactor of this invention can give a high yield to products from a reaction zone of about equal to or less than 18 inches long. Conventional prior art reactors are 10 to 30 times longer, making them impractical for use in portable units. While the reactor of this invention may be scaled up to produce greater volumes of product, even to the point that the reactor is no longer portable, such increase is expected to be accomplished by adding modules or cells, rather than appreciably increasing the size of the reaction chambers.

A presently preferred configuration of this inventive reactor uses an air pump, if air is one of the reactants; a storage tank for another of the reactants, if appropriate; a pump for water or other liquid into which the product is to be dissolved or absorbed, if appropriate; a high-temperature reactor thermally insulated and suitably shaped (for example, substantially in the form of a cube) for minimum consumption and loss of energy; an absorber system to collect product, if gaseous, from the reactor and place it into a liquid at high efficiency; an exhaust gas purifier; and a control system using gauges, valves, sensors, and electrical circuits for positive, safe operation. The system can be sufficiently small to be mounted on a skid or a trailer, and only the reactants, the liquid and either electricity or fuel for an electrical generator are required to permit on-site and on-demand generation of the product dissolved in a flowing liquid stream. With this invention, there is no need to produce a concentrated liquid product, thus avoiding any inherent hazards that might be present with the product in that form. The system may also be sufficiently large so that it would be part of a permanent installation.

BRIEF DESCRIPTION OF THE DRAWINGS

These and other aspects of the invention will be more fully understood from the following detailed description taken in conjunction with the accompanying drawings, in which.

DETAILED DESCRIPTION OF THE INVENTION

Figure 1:
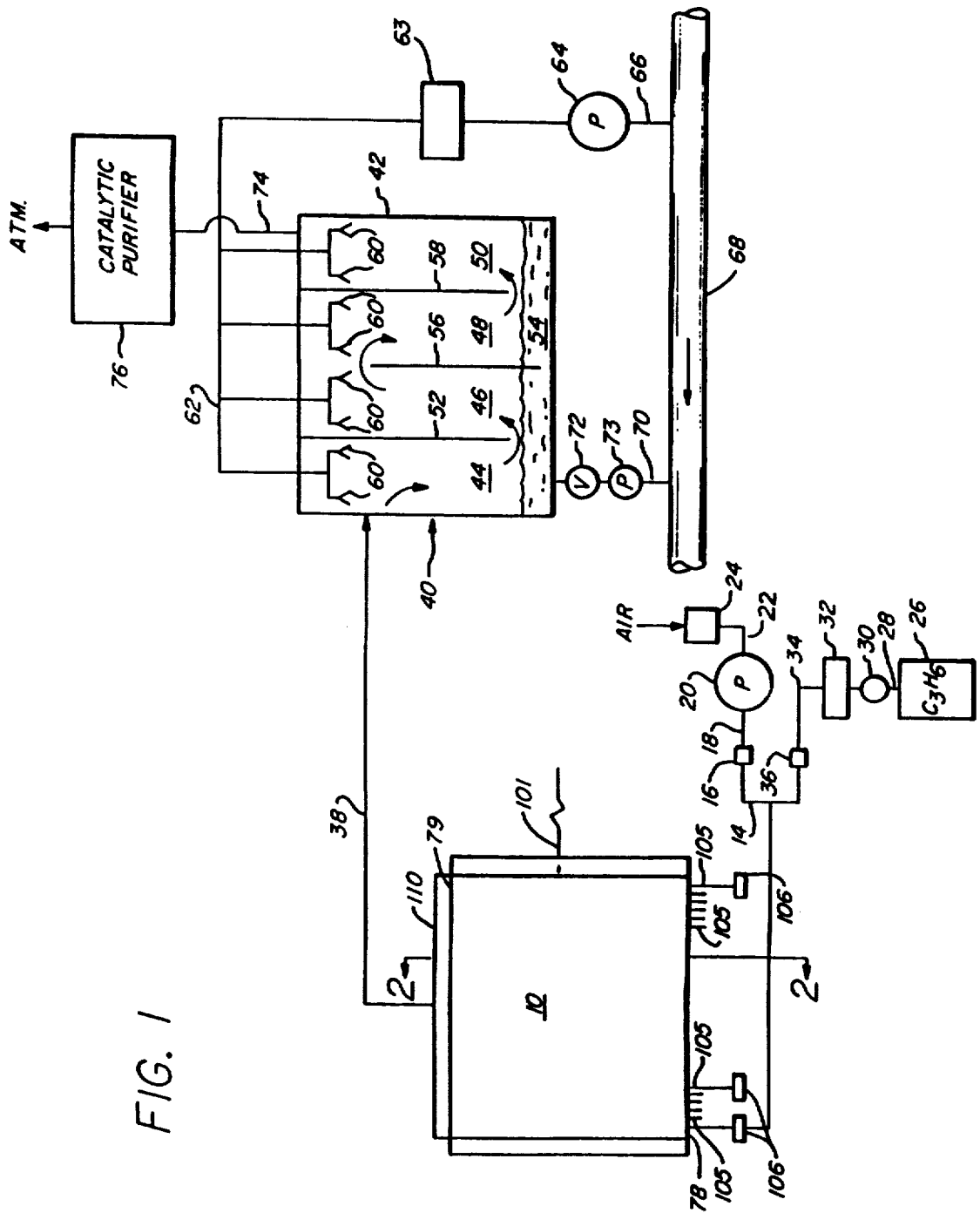
FIG. 1 schematically shows the reactor of this invention connected to receive a mixture of two gases, and to discharge the reaction products into an absorber.

It has been discovered that a relatively small, modular reactor can be devised, which may be easily moved from place to place to catalytically produce various chemical products. In one embodiment, the reactor is an apparatus for making an organic product from at least two reactants, the apparatus having a catalyst chamber with an inlet and an outlet. A permeable bed of catalyst support particles is in the chamber between the inlet and the outlet, and a catalyst which promotes the reaction of the reactants to form the product is present on at least some of the particles. A mechanism is provided for introducing the reactants through the inlet to the reaction chamber, and another mechanism is provided for removing the organic product from the reaction chamber through the outlet. Although it is conceivable that the reactor of the present invention may find utility in the production of inorganic materials, it is expected that it will find more applications in the manufacture of organic compounds.

The apparatus capable of serving as the reaction chamber can have various shapes, such as cylindrical or rectangular blocks, each containing hollow passageways capable of containing the catalyst and the reaction. These passageways may be tubular in nature, or they may be configured as to form a fixed-bed chamber, or numerous single tubes can be assembled in various arrays. Spouted beds or fluidized reactor zones could also be used. However, many of these reaction chamber types have inefficient temperature/heating characteristics, or serious channelling of unreacted starting material gases often occurs.

A preferred apparatus for making acrolein includes a reactor of this invention with at least one pair of substantially parallel plates disposed side-by-side. Each plate includes catalyst or reaction chambers which each have a respective inlet and outlet. A catalyst in each chamber promotes the reaction, for example, the oxidation of propylene to acrolein, and a mechanism is provided for introducing the reactants, such as a mixture of propylene and oxygen, into the catalyst chambers through the inlets. A heating element or panel between the plates heats the reactants and the catalyst to a temperature which causes the reactants to react with each other in the presence of the catalyst to form the reaction products. A mechanism is also provided for removing the reaction products from the outlets of the catalyst chambers.

In a preferred embodiment, each plate is in the shape of a rectangular slab having major sides many times greater than the thickness of the slab. The slab has a first minor end and a second minor end opposite the first minor end. For example, each plate may be a rectangular slab about 1' thick, with opposing major faces each being approximately square and having a dimension of about 18' on each side. A plurality of elongated and laterally spaced bores extend through each plate in a direction substantially parallel to the major faces of the plate beginning at the first minor end and terminating at the second minor end, to provide as many as 20 to 30 parallel catalyst chambers in each plate. The reaction chambers may be said to extend from one minor end to an opposing minor end on opposite sides of the plate, beginning at one end with their inlet and terminating at the other with their outlet.

A thin, panel-shaped flat heating element is sandwiched between adjacent major faces of a pair of plates to form a heated pair, or cell, the temperature of which is controlled by a thermostat mounted in a face of one of the plates adjacent the heating element. Preferably, heat insulation around the assembled plates which form the reactor limits the amount of external energy which must be applied to the apparatus. A separate respective capillary tube is connected at one end to a respective catalyst or reaction chamber inlet, and at the other end to a reactant supply pipe, which supplies a mixture of reactants to each catalyst chamber inlet through a respective capillary tube. These capillary tubes are fed by a common header containing pressurized mixed starting materials. This arrangement uses frictional drag in the tubes to control the flow rates through each of the separate reaction chambers. Although capillaries are preferred for flow control, other devices, such as orifices or adjustable valves, may also be used.

A separate elongated collection header over the outlets of the catalyst chambers in each plate collects reaction products leaving the reaction chambers. Each of the catalyst chambers is packed with a bed of catalyst which preferentially promotes the reaction, such as the oxidation of propylene to acrolein.

The presently preferred embodiment of the invention includes a plurality of pairs of parallel plates, each pair being constructed and arranged with a panel-shaped heating element as described above. A sufficient number of the pairs of plates are staked together to form an array, or a reactor, essentially in the shape of a cube to minimize heat loss. In another embodiment, the plates could be curved or flat and arranged concentrically. The space between adjacent pairs of plates is thermally insulated to provide good temperature control in each pair of plates served by a respective panel-shaped heating element.

Preferably, the plates are made of a metal selected from the group of aluminum, tantalum, titanium, tungsten, niobium or mixtures thereof, or at least the inner surfaces of the reaction chambers are made from these metals. It is additionally preferred that all internal surfaces contacted by the gases and/or liquids passing through the catalyst chambers and collection headers, absorber, if present, and conduits connecting the headers and absorbers or other pieces of equipment are made of metals selected from that group. It is possible that some tubing and conduits not subject to high temperatures may be made from inert polymeric plastics, elastomers and the like.

The cross-sectional area of each chamber is between 0.70 and 3.0 cm$^2$, and preferably is in the range of about 1.2 to 1.7 cm$^2$.

Suitable mechanisms are provided for sensing the temperature of the catalyst and controlling the heat supplied by the heaters to keep the catalyst temperature within its operating range. Of course, if the expected reaction temperature range exceeds the softening point of the metal used to line the reaction chambers, for example of aluminum, one should plan to use a different material selected from the above-enumerated list.

A preferred form of the invention also includes a pump for taking a stream of liquid from a source of liquid which is to be treated with the reaction product. Spray nozzles connected to the pump outlet, or other source of liquid under pressure, spray liquid into an absorber, through which the reaction products from the catalyst chambers pass. The reaction product is absorbed in the liquid stream from the liquid supply, and added to the system which is to be treated, either as a stream diluted by the system to be treated, or undiluted if the system to be treated is composed wholly of the product stream from the reactor. If gases are a product, those which are not absorbed in the liquid sprayed into the absorber pass through a catalytic purifier.

The reactor of this invention has been successfully used to catalytically produce (1) acrolein from air and propylene; (2) methacrolein from isobutylene and air; and (3) acrylonitrile from propylene and ammonia. The example of making acrolein from propylene and air will be used from time to time throughout this description as representative of an actual use of the reactor, but the invention should not be limited to this example. It is anticipated that the reactor of this invention will find utility in the production of organic chemicals other than those enumerated above.

Referring to FIG. 1, a reactor 10 in the general shape of a cube receives a gas mixture of air, as one reactant, and propylene, as the other reactant, from a plurality of horizontal and parallel supply lines 12 (see FIG. 2), each connected at respective inlet ends through a respective T-joint 14 to the discharge of a respective air pressure regulator 16, the inlet of which is connected by an air manifold line 18 to the discharge of air pump 20 having an inlet 22 connected to a filter 24, through which air is drawn.

A tank of one of the reactants, propylene for example, has a discharge line 28 connected through a primary pressure regulator 30 and a filter 32 to a gas supply line 34 connected through a secondary pressure regulator 36 to the T-joint 14. Obviously, if liquid reactants are used, these gaseous sub-systems would be replaced by the liquid tanks, supply lines, etc.

Reaction products from the upper side of the reactor are carried by a delivery pipe 38 (see FIG. 1) to an absorber 40, which includes a housing 42 divided into first, second, third and fourth absorption zones 44, 46, 48 and 50, respectively. A first vertical baffle 52 extends from the top of the housing 42 downwardly to terminate just above a pool 54 of liquid, which may be water, fuel, or other liquid which absorbs acrolein. A second vertical baffle 56 mounted in the housing parallel to, and spaced horizontally from, the first baffle extends from below the level of liquid pool 54 and a short distance below the top of the housing. A third vertical baffle 58 parallel to, and spaced from, the second baffle extends from the top of the housing down to terminate just above the surface of the liquid pool 54. Each of the baffles extends entirely across the housing in a direction perpendicular to the plane of FIG. 1 so that the three baffles divide the housing 42 into the four absorption zones 44, 46, 48 and 50.

A separate respective group of spray nozzles 60 mounted in the upper end of each absorption zone are supplied liquid from a liquid supply pipe 62 connected through a pressure regulator 63 to the discharge of a pump 64, which has as its inlet connected through a suction pipe 66 to a main body or stream of liquid flowing through a main pipe 68. Line 66 and pump 64 may be replaced by other suitable sources, such as pressurized water lines typical of fire hydrants and hose bib stand pipes. In any event, the pressure of the incoming fluid is determined by a pressure regulator 63, or other suitable flow-monitoring device.

A drain pipe 70 extends from the liquid pool 54 in the housing through a control valve 72 and a return pump 73 to return product-containing liquid in the absorber to the main pipe 68. Alternatively, the product-containing liquid may be sent to storage for future use.

An exhaust conduit 74 carries unabsorbed gases from the upper end of the fourth absorption zone 50 to a catalytic purifier 76, which oxidizes the remaining hydrocarbons and any carbon monoxide to water and carbon dioxide, which are discharged to the atmosphere. Obviously, if the product is a liquid or is condensed to a liquid, the equipment for handling the product and placing it into useful solutions or other forms will be different.

Figure 2:
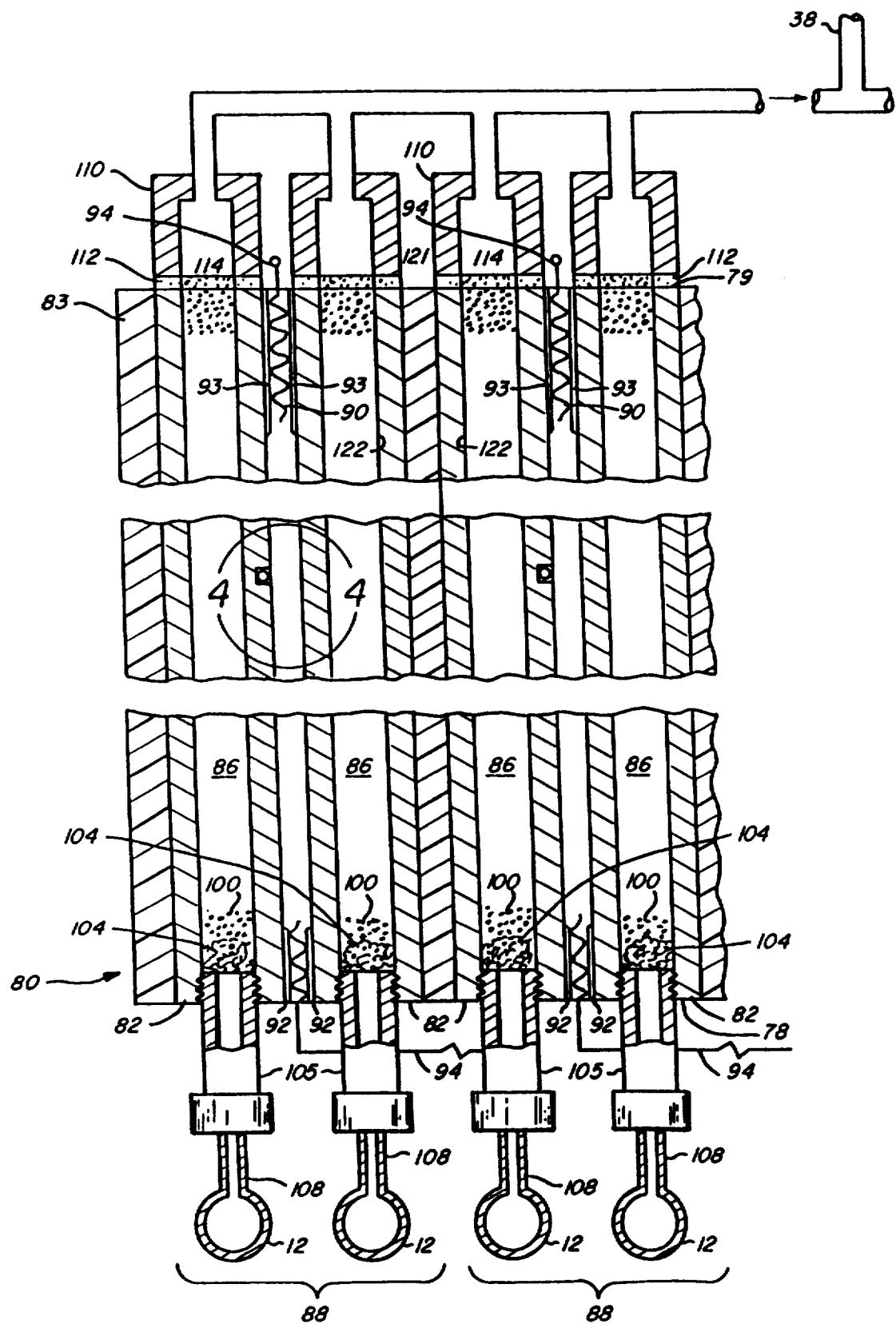
FIG. 2 is a view taken on line 2—2 of FIG. 1 showing details of the reactor in cross-section.
Figure 3:
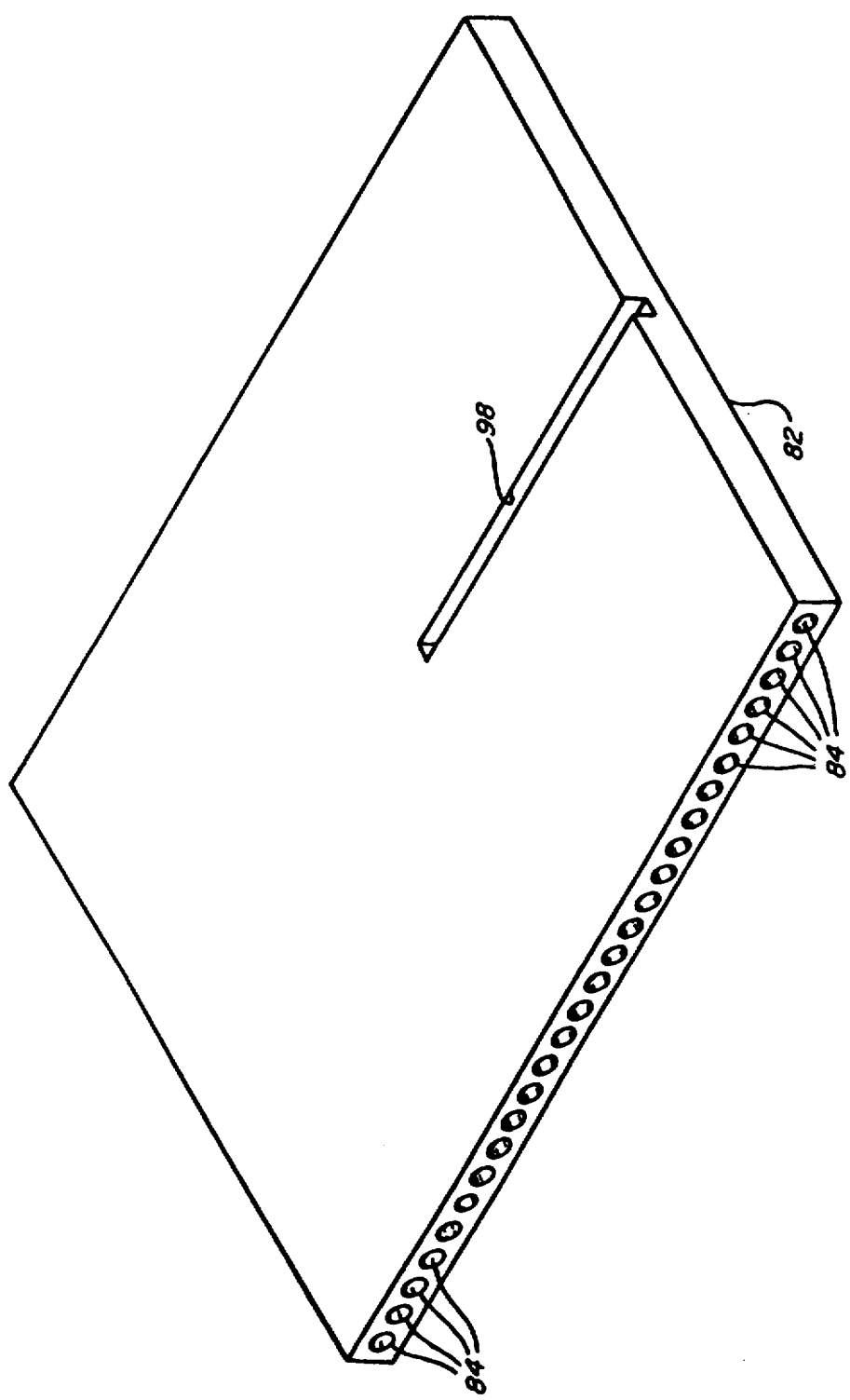
FIG. 3 is a perspective view of one of the parallel plates in the reactor.

As shown in FIG. 2, the reactor 10 may be a sandwich assembly or array 80 of a plurality of flat, rectangular plates or slabs 82 disposed side-by-side so the reactor is substantially in the shape of a cube to minimize heat loss from a given volume for the reactor. A layer 83 of thermal insulating material surrounds the reactor to reduce heat loss and energy consumption. Each plate 82 has a first minor end 78 containing the inlets to the reactor plate, and a second minor end 79 opposite the first minor end containing the outlets. First minor end 78 and second minor end 79 are generally perpendicular to the major face of slab 82.

Although the plates may be of any suitable dimensions, a successful reactor has been designed in which the plates are about 18"×18"×1". The plates are assembled with their major surfaces vertically oriented to form the assembly 80 shown in FIG. 2. A plurality of vertical bores 84 extend through each plate. If the plate is about 1" thick, it has been found that bores about ⅛" in diameter, and located on about ⅛" centers form properly spaced and dimensioned reaction chambers 86 (FIG. 2).

Figure 5:
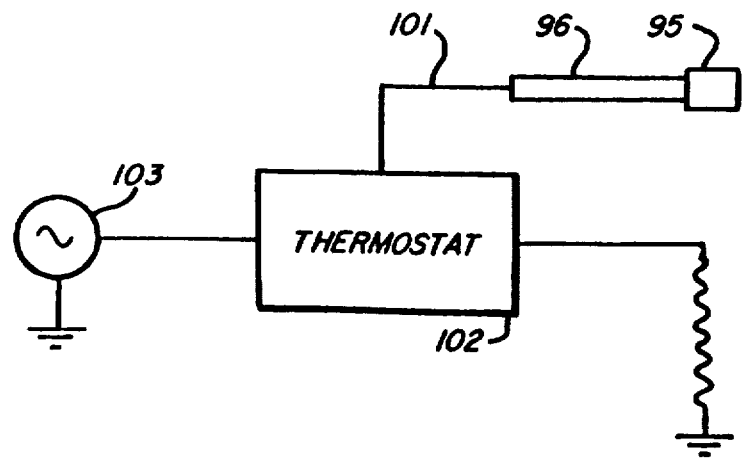
FIG. 5 is a schematic diagram showing a circuit for controlling the temperature of the catalyst in the reactor.

The plates may be arranged in pairs 88 (FIG. 2), with a separate, respective, flat electrical heating panel 90 disposed between adjacent faces 92 of each plate in each pair. A pair of plates with a heating panel 90 between them may be referred to as a cell. A thin, separate, respective sheet 93 of ceramic insulation is between each face of each electric panel and the adjacent face of a plate. The thin sheet of ceramic insulation, which can be of any suitable thickness, say 0.03 to 0.07", provides a more uniform transfer of heat from the electric heating panels 90 to the entire adjacent surfaces of the plates. Electrical power leads 94 (FIGS. 2 and 5) supply power to the heater panels. Alternatively, the reactor could consist simply of one plate 82 and one adjacent flat electrical heating panel 90.

Figure 4:
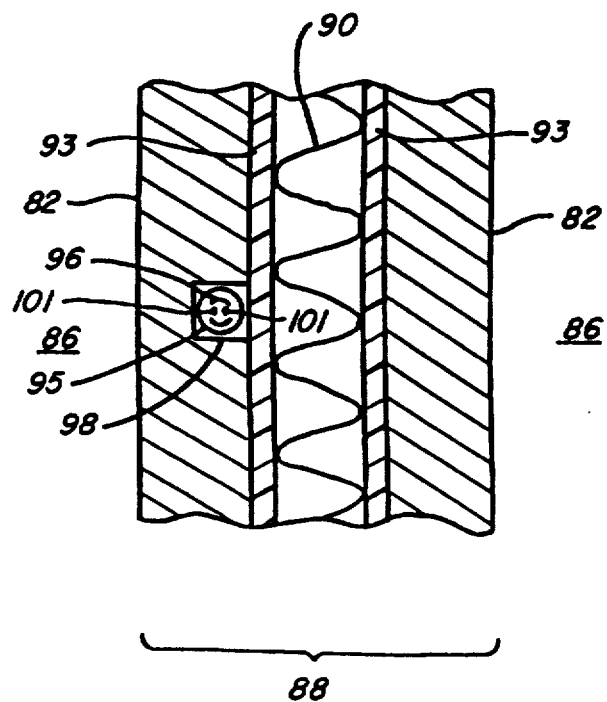
FIG. 4 is an enlarged view taken in the area 4—4 of FIG. 2.

A thermocouple 95 on the inner end of a horizontal support 96 (FIGS. 4 and 5) in a horizontal groove 98 extending from about the center of one vertical edge of a plate in each pair to about the center of that plate, and opening toward the other plate in the pair, senses the temperature of the plates surrounding the respective reaction chambers 86, each of which is filled with a bed 100 of a catalyst which promotes the oxidation, or other reaction, of the reactant, such as propylene, to form the product, such as acrolein. A separate pair of electrical signal leads 101 (see FIGS. 4 and 5) extend from each respective thermocouple to a respective adjustable thermostat 102, which controls the amount of electrical power supplied from a generator 103 to a respective electrical heater panel 90 to keep the catalyst in the adjacent reaction chamber 86 at the required operating temperature.

A separate, respective loose plug 104 (FIG. 2) of quartz wool in the bottom of each reaction chamber 86 rests on the upper end of a separate, respective short nipple 105 threaded into the lower end of a respective reaction chamber to form a reaction chamber inlet. The upper end of a separate, respective capillary tube 108 is sealed at its lower end to a respective gas supply pipe 12. The capillary tubes act as flow control devices and may be of any suitable internal diameter for that purpose. Capillary tubes with an inside diameter of about 0.007" provides good flow control and distribution of reactant gas from the supply pipes 12.

A separate, elongated, rectangular header 110 rests on a separate, respective graphite gasket 112 on the upper edge of each plate and over the upper (outlet) ends of the reaction chamber in each plate to collect reaction products which flow up through the reaction chambers, through respective holes 114 in the gaskets 112, and to the delivery pipe 38 (see FIGS. 1 and 2).

The reactor plates and all other components with surfaces contacted by the reaction products should be made of a material which has good thermal conductivity, and which does not adversely affect the production of the desired product. For example, to produce acrolein by oxidizing propylene, aluminum is preferred because of its relatively low cost. Other metals, such as tantalum, titanium, tungsten, niobium or mixtures of these, may also be used. The term "mixtures" as used herein includes alloys of the above-listed metals with each other as well as other ways in which the various suitable metals may be mixed, such as simply being blended or used physically adjacent one another. Aluminum alloys of the 6000-type are preferred because they are inert, machinable, and can be welded. These are unusual materials for reactors, but have been found to be particularly advantageous for catalytic oxidation reactions. The use of ferrous metals within the reactor decreases the selectivity of the process to acrolein, if that is the reaction run. Brass, bronze and copper are also not used because they deteriorate chemically when contacted with such reactants as air and propylene. We are not aware of any prior art use of aluminum equipment, except for the single report of the use of aluminum tubes that were coated with copper as a catalyst described by Xing and Inoue, *Kagaku Kogaku Ronbunshu*, Vol. 10, No. 4, p. 439–45 (1984).

A separate respective panel 121 of thermal insulation between the adjacent outer faces 122 of each adjacent pair of plates provides good temperature control for each pair of plates served by a respective heating panel 90. The panels may be of any suitable material, such as sandstone, refractory material, spun glass, and the like. Each panel has sufficient thickness to reduce thermal flow between reactor pairs 88. Although asbestos, asbestos-filled materials such as magnesia, and transite can provide adequate protection against thermal convention, their use is discouraged due to possible environmental health hazards.

The operation of the reactor will now be described using the production of acrolein as illustrative only. With the reactor packed with beds of supported catalyst, as described above and shown in FIG. 2, a mixture of air and propylene in a ratio of 84:16, respectively, by volume, was fed into the inlets of the reaction chambers, which were heated to about 410° C. The pressure in the reaction chambers was between about 2 and about 5 lbs./in.$^2$, and the flow rate per unit of cross-sectional area was about 100 ml/min./cm$^2$. The effluent from the reaction chambers 86 flowed through the aluminum headers and the aluminum delivery pipe 38, which were surrounded by a layer of insulation (not shown) to keep the gas in them at a temperature above about 60° C. to prevent premature condensation of acrolein, and into the upper end of the first absorption zone of the absorber. The effluent was contacted in the first absorber zone by a spray of water supplied by pump 64 to the spray nozzles. The intake of the pump was connected to main pipe 68 carrying a main stream of water to be treated with acrolein. Water droplets with absorbed acrolein fell into the pool 54 in the bottom of the absorber. Unabsorbed gases passed under the first baffle 52 and into the bottom of the second absorption zone following the arrows shown in FIG. 1, rising to meet more water droplets sprayed into the top of that zone. Additional acrolein was absorbed and carried to the pool in the bottom of the absorber. The unabsorbed gases continued over the top of the second baffle into the top of the third absorption zone for additional absorption of acrolein, and passed under the third baffle to flow up through the spray of water in the fourth absorption zone, and out the exhaust conduit 74 through the catalytic purifier, 76, where any carbon monoxide and unreacted hydrocarbons were oxidized to carbon dioxide and water vapor, which were discharged into the atmosphere.

The water sprayed into the absorber scrubbed more than 99.9% of the acrolein from the reactor effluent, and carried it into the liquid pool in the bottom of the absorber, where the acrolein-rich water was removed through the drainpipe 70 and returned to the main stream of water downstream of the pump inlet.

In the example just described, the concentration of the acrolein in the water pool in the bottom of the absorber was about 0.2%, by weight, and it was returned to the main water stream at a rate to give a treated solution with between about 1 and about 15 ppm acrolein for weed control in ditches through which the treated water flowed. Approximately the same concentration would be used for treating injection wells for secondary recovery of oil, or maintenance of gas pressure in an underground formation. In either case, the reactive nature of the acrolein in the dilute solution causes the acrolein to substantially disappear within a few days.

The acrolein added to water for secondary recovery can scavenge hydrogen sulfide ($H_2S$) and destroy microbes (e.g., anaerobic bacteria which consume sulfur, say from calcium sulfate which may be available in the injection water or in the formation, and convert it to $H_2S$, a corrosive compound), which may be in either the treated water, or downhole, or both.

As noted, the water or other fluid supplied to the absorber may come from a pressurized source, in which case the pump is not required. The water to be treated can come from a source of irrigation water, or water to be injected into an underground formation, and either all of the water to be treated can be passed through the absorber, which would be operated to give the required final concentration of acrolein, or only a portion of the water may be passed through the absorber and then recombined with the rest of the water, as described above. It is possible to operate the absorber to produce a solution which contains up to about 25% acrolein by weight.

It has been determined that in building a compact, portable reactor of the type described above, and in which a highly-divided catalyst is employed, it is advantageous in one embodiment to limit the cross-sectional area of each reaction chamber 86 to about 2 cm$^2$ or less, and to limit the flow rate of reactants to about 150 cc/min./cm$^2$ of cross-sectional area or less. Accordingly, to obtain a given throughput of reactants for a desired output of product, a number of reaction chambers were grouped together, i.e. placed in parallel, as described above to permit accurate control of flow rate and temperature for each chamber. The number of parallel reaction chambers may be quite large to obtain a relatively large throughput of reactants and production of product, and the number of chambers may be sufficiently large as to make the reactor no longer portable. The same result cannot be obtained by simply using a reactor with a large, undivided cross-sectional area equal to the total of the group of parallel reaction chambers. The yield of product with the large, undivided cross sectional area is inevitably low and, therefore, uneconomic. In operating the reactor of this invention as described above at 410° C., with a feed mixture of 16% propylene and 84% air, the discharge from the reactor was 9.4% acrolein, resulting in a yield of approximately 68% of the propylene to acrolein.

Many modifications may be made in the apparatus of the present invention without departing from its spirit and scope, which are defined only in the appended claims. For example, one skilled in the art may find that certain geometric configurations of the flat plates, or certain alloys of the preferred metals give particularly advantageous results. From the foregoing description, it will be seen that this invention provides a portable, self-contained system for generating chemicals on demand and on-site to produce dilute, safe solutions thereof.

We claim:

1. A reaction assembly for the production of reaction products selected from the group consisting of acrolein, methacrolein, and acrylonitrile absorbed and carried in a carrier fluid, comprising:
   A) a source of first reactant gas, the first reactant gas selected from the group consisting of air and ammonia;
   B) a source of hydrocarbon-containing second reactant gas, the second reactant gas selected from the group consisting of propylene and isobutylene;
   C) a fixed bed reactor for holding a catalyst suitable to facilitate a chemical reaction between the first reactant gas and the second reactant gas to produce a reaction product, comprising:
      1) at least one plate presenting a generally planar face and first and second generally parallel ends;
      2) a plurality of reaction chambers in the plate presenting interior surfaces made of a metal selected from the group consisting of aluminum, tantalum, titanium, tungsten, niobium and mixtures thereof, with each chamber having a porous bed of catalyst materials contained therein and a pair of porous end caps in each chamber for holding the catalyst bed in the chamber in a compacted state while enabling the flow of gases through the chamber, said chambers extending within the plate with their longitudinal axes generally parallel to each other from inlet ports generally adjacent the first end of the plate for receiving reactant gases to outlet ports generally adjacent the second end of the plate for discharge of reaction products as produced in the chambers; and
      3) at least one heating panel generally adjacent and parallel to the planar face of the plate;
   D) an absorber receiving reaction products from said reactor and carrier fluid from a source thereof, said absorber exposing the reaction products to the carrier fluid for enabling at least some of the reaction products to be absorbed into the carrier fluid; and
   E) a conduit in fluid communication with the absorber for flow of carrier fluid with reaction products absorbed therein from the reaction assembly.

2. The reaction assembly of claim 1 wherein said plates are arranged in pairs with their planar faces facing one another, and where one heating panel is present between the facing planar faces; each pair of plates and heating panel therebetween comprising a cell.

3. The reaction assembly of claim 2 having the absence of a heating panel between adjacent cells.

4. The reaction assembly of claim 2 wherein a thermostat is present in the planar face facing the heating panel of one of the plates in the cell.

5. The reaction assembly of claim 1 wherein the metal plate is made from a material selected from the group consisting of aluminum, tantalum, titanium, tungsten, niobium and mixtures thereof.

6. The reaction assembly of claim 1 where the cross-sectional area of each reaction chamber is between 0.70 and 3.0 cm$^2$.

7. The reactor assembly of claim 1 where the reaction chambers are about 18" long.

8. The reactor assembly of claim 1 where the plate is approximately 1" thick.

9. The reactor assembly of claim 1 where plates may be added to or removed from the reactor to make the reactor assembly modular.

10. A reaction assembly for the production of reaction products selected from the group consisting of acrolein, methacrolein, and acrylonitrile absorbed and carried in a carrier fluid, comprising:
   A) a source of first reactant gas, the first reactant gas selected from the group consisting of air and ammonia;
   B) a source of hydrocarbon-containing second reactant gas, the second reactant gas selected from the group consisting of propylene and isobutylene;
   C) a fixed bed reactor for holding a catalyst suitable to facilitate a chemical reaction between the first reactant gas and the second reactant gas to produce a reaction product, comprising:
      1) a plurality of plates, each plate presenting a generally planar face and first and second generally parallel ends, where plates may be added to or removed from the reactor, and where the plates are arranged in pairs with their planar faces facing one another, and where one heating panel is present between the facing planar faces, each pair of plates and heating panel therebetween comprising a cell;
      2) a plurality of reaction chambers in the plate presenting interior surfaces made of a metal selected from the group consisting of aluminum, tantalum, titanium, tungsten, niobium and mixtures thereof, with each chamber having a porous bed of catalyst materials contained therein and a pair of porous end caps in each chamber for holding the catalyst bed in the chamber in a compacted state while enabling the flow of gases through the chamber, said chambers extending within the plate with their longitudinal axes generally parallel to each other from inlet ports generally adjacent the first end of the plate for receiving reactant gases to outlet ports generally adjacent the second end of the plate for discharge of reaction products as produced in the chambers; and 3) at least one heating panel generally adjacent and parallel to the planar face of the plate;

D) an absorber receiving reaction products from said reactor and carrier fluid from a source thereof, said absorber exposing the reaction products to the carrier fluid for enabling at least some of the reaction products to be absorbed into the carrier fluid; and E) a conduit in fluid communication with the absorber for flow of carrier fluid with reaction products absorbed therein from the reaction assembly.

11. The reaction assembly of claim 10 wherein a thermostat is present in the planar face facing the heating panel of one of the plates in the cell.

12. The reaction assembly of claim 10 wherein the metal plate is made from a material selected from the group consisting of aluminum, tantalum, titanium, tungsten, niobium and mixtures thereof.

13. The reaction assembly of claim 10 where the cross-sectional area of each reaction chamber is between 0.70 and 3.0 cm$^2$, the reaction chambers are about 18" long and where the plate is approximately 1" thick.

14. The reaction assembly of claim 10 having the absence of a heating panel between adjacent cells.

* * * * *

UNITED STATES PATENT AND TRADEMARK OFFICE
CERTIFICATE OF CORRECTION

PATENT NO. : 5,304,354
DATED : April 19, 1994
INVENTOR(S) : Finley, et. al.

It is certified that error appears in the above-indentified patent and that said Letters Patent is hereby corrected as shown below:

Title page, item [73], Assignee: "Baker Hughes Incorporated, Houston, Tex" should be deleted--.

Signed and Sealed this

Thirtieth Day of August, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,304,354

DATED : April 19, 1994

INVENTOR(S) : Charles M. Finley, Charles L. Kissel

It is certified that error appears in the above-identified patent and that said Letters Patent is hereby corrected as shown below:

On the title page:

ITEM: [56] References Cited – U.S. PATENT DOCUMENTS delete the following references:

| | | | |
|---|---|---|---|
| 4,400,465 | 8/1983 | Morihara et al. | 435/68.1 |
| 4,608,364 | 8/1986 | Grau | 514/4 |
| 4,701,440 | 10/1987 | Grau | 514/3 |
| 4,916,212 | 4/1990 | Marhussen | 435/69.4 |
| 4,946,828 | 8/1990 | Marhussen | 514/3 |
| 4,959,351 | 9/1990 | Grau | 514/3 |
| 5,008,241 | 4/1991 | Markussen et al. | 514/3 |
| 5,028,586 | 7/1991 | Balschmidt et al. | 514/3 |
| 5,028,587 | 7/1991 | Dorschug et al. | 514/3 |

On the face of the patent at [56] References Cited – OTHER PUBLICATIONS delete the following references:

Blundell et al., *Advances in Protein Chemistry*, 26: 340–347 (Ed. Anifinsen, Edsall, Richards), 1972.
Weinert M. et al., *Hoppe-Seyler's Z-Physiol. Chem.*, 352: 719–724, 1971.
Zahn et al., "*Molecular Basis of Insulin-Action*", 5th Anniversary Insulin Symposium, Indiana, Oct. 1971.
Smith, L., "Amino Acid Sequences of Insulin", Sec. III The Molecular Basis of Action, 5th Anniversary Insulin Symp. 1971.
Dayhoff, M., Atlas of Protein Sequence and Structure, vol, 5:89–99, 1972.
Creighton, T., *Proteins*, Watt. Freeman & Co., 1984, p. 428.

At column 3, line 49, please delete "1'" and insert --1"-- therefor.

UNITED STATES PATENT AND TRADEMARK OFFICE
CERTIFICATE OF CORRECTION

PATENT NO.   :   5,304,354                              Page 2 of 2
DATED        :   April 19, 1994
INVENTOR(S)  :   Charles M. Finley, Charles L. Kissel It is certified that error appears in the above-identified patent and that said Letters Patent is hereby corrected as shown below:

At column 3, line 51, please delete "18'" and insert ---18"--- therefor.

At column 7, line 2, please delete "provides" and insert ---provide--- therefor.

At column 8, line 16, please delete "upreacted" and insert ---unreacted--- therefor.

Signed and Sealed this

Sixteenth Day of May, 1995

Attest:

BRUCE LEHMAN

*Attesting Officer*          *Commissioner of Patents and Trademarks*